US00PP16150P2

(12) United States Plant Patent
Bellinger

(10) Patent No.: US PP16,150 P2
(45) Date of Patent: Dec. 6, 2005

(54) ***PHILODENDRON* PLANT NAMED 'VARIEGATED SPORT #1'**

(50) Latin Name: *Philodendron hybrid*
Varietal Denomination: Variegated Sport #1

(76) Inventor: Hartwig Paul Bellinger, 106 Ungram Cir., Longwood, FL (US) 32779

( * ) Notice: Subject to any disclaimer, the term of this patent is extended or adjusted under 35 U.S.C. 154(b) by 6 days.

(21) Appl. No.: 10/949,946

(22) Filed: Sep. 24, 2004

(51) Int. Cl.[7] ..... A01H 5/00

(52) U.S. Cl. ..... Plt./381

(58) Field of Search ..... Plt./381

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Philodendron* plant named 'Variegated Sport #1', characterized by its upright and outwardly spreading plant habit; dark burgundy-colored stems; glossy leaves that are initially yellow green with dark reddish brown variegation; and excellent postproduction longevity.

3 Drawing Sheets

Botanical classification/cultivar designation: *Philodendron* hybrid cultivar Variegated Sport #1.

BACKGROUND OF THE INVENTION

The present invention relates to a new and distinct cultivar of *Philodendron* plant, botanically known as *Philodendron* hybrid, and hereinafter referred to by the name 'Variegated Sport #1'.

The new *Philodendron* is a naturally-occurring whole plant mutation of the *Philodendron* hybrid cultivar Prince of Orange, disclosed in U.S. Plant Pat. No. 6,797. The new *Philodendron* was discovered by the Inventor in a controlled environment in Apopka, Fla., as a single plant within a group of plants of 'Prince of Orange' during the summer of 2000. The selection of this plant was based on its uniquely-colored leaves.

Asexual propagation of the new cultivar by stem cuttings and tissue culture in a controlled environment in Apopka, Fla., since the spring of 2002, has shown that the unique features of this new *Philodendron* plant are stable and reproduced true to type in successive generations of asexual propagation.

BRIEF SUMMARY OF THE INVENTION

The new *Philodendron* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Variegated Sport #1. These characteristics in combination distinguish 'Variegated Sport #1' as a new and distinct cultivar:

1. Upright and outwardly spreading plant habit.
2. Dark burgundy-colored stems.
3. Glossy leaves that are initially yellow green with dark reddish brown variegation.
4. Excellent postproduction longevity.

Plants of the new *Philodendron* are most similar to plants of the parent, the cultivar Prince of Orange. Plants of the new *Philodendron* differ primarily from plants of the cultivar Prince of Orange in developing leaf coloration as plants of the cultivar Prince of Orange have young leaves that are dark bronze in color.

Plants of the new *Philodendron* can also be compared to plants of the cultivar Pastel Sport #2, disclosed in a U.S. Plant patent application Ser. No. 10/949,932. In side-by-side comparisons conducted in Apopka, Fla. plants of the new *Philodendron* differed from plants of the cultivar Pastel Sport #2 primarily in leaf coloration.

BRIEF DESCRIPTION OF THE PHOTOGRAPHS

The accompanying colored photographs illustrate the overall appearance of the new *Philodendron*, showing the colors as true as it is reasonably possible to obtain in colored reproductions of this type. Colors in the photographs may differ slightly from the color values cited in the detailed botanical description which accurately describe the colors of the new *Philodendron*.

The photograph on the first sheet comprises a top perspective view of a typical plant of the cultivar Variegated Sport #1 grown in a container.

The photograph on the second sheet comprises a top perspective view of a typical plant of the parent, the cultivar Prince of Orange, grown in a container.

The photograph on the third sheet comprises a close-up view of the lower surfaces of a fully expanded leaf (left) and a developing leaf (right) of the cultivar Variegated Sport #1.

DETAILED BOTANICAL DESCRIPTION

The aforementioned photographs and the following observations and measurements describe eight-month old plants grown in 20-cm containers in Apopka, Fla., in a polyethylene-covered greenhouse with day temperatures of 21 to 32° C., night temperatures of 21 to 29° C., and light levels about 1,500 foot-candles.

In the following description, color references are made to The Royal Horticultural Society Colour Chart, 1995 Edition, except where general terms of ordinary dictionary significance are used.

Botanical classification: *Philodendron* hybrid cultivar Variegated Sport #1.

Parentage: Naturally-occurring whole plant mutation of *Philodendron* hybrid cultivar Prince of Orange, disclosed in U.S. Plant Pat. No. 6,797.

Propagation:

*Method.*—By tissue culture.

*Time to initiate roots on a meristem-cultured plant.*—About 16 weeks at day temperatures of 32° C. and night temperatures of 21° C.

*Time to develop roots on a meristem-cultured plant.*—About 20 weeks at day temperatures of 24° C. and night temperatures of 18° C.

*Root description.*—Strong, thick and fleshy; roots whitish, towards the apex, dark burgundy.

Plant description:

*Plant shape.*—Upright and outwardly spreading plant habit, inverted triangle, symmetrical; rosette growth habit.

*Growth habit.*—Leaves closely spaced, bushy and dense growth habit.

*Plant height.*—About 32 to 38 cm.

*Plant diameter or spread.*—About 65 to 77 cm.

*Stem description.*—Length, from soil level to growing point: About 10 cm. Diameter: About 2.5 to 3 cm. Internode length: About 5 to 10 mm. Color: 187A; leaf scars, 195A.

*Foliage description.*—Length: Largest leaves, about 32 cm; average leaves, about 24 to 27 cm. Width: Largest leaves, about 16 cm; average leaves, about 13 cm. Thickness: About 0.8 mm. Shape: Ovate. Apex: Acute. Base: Hastate. Margin: Entire. Aspect: Leaf blade held about 45° from vertical. Texture, upper and lower surfaces: Leathery; glabrous; glossy. Venation: Midvein straight and thick; midvein and primary veins recessed into the upper surface and protruding from the lower surface. Color, newly expanded leaves, upper surface: 153A to 153B; variegation, 34B; midrib, 153A streaked with 34A to 34B; primary veins, 34B. Color, newly expanded leaves, lower surface: 145B to 145C; dense variegation, 178A; midrib, 179A streaked with 180B; primary veins, 178A. Color, expanded leaves (center of plant), upper surface: Darker and greener than but closest to 144A; variegation, 177A and 178B; midrib, 144A streaked with 178A; primary veins, 178A. Color, expanded leaves (center of plant), lower surface: 144A to 144B; variegation, 177A; midrib, 178A streaked with 179B; primary veins, 178A. Color, mature leaves (lowermost on plant), upper surface: Lighter than but closest to 137A; midrib, 146C; primary veins, 146D. Color, mature leaves (lowermost on plant), lower surface: Darker than but closest to 144A; midrib, 178A to 178B; primary veins, 144A tinged with 178B. Petioles: Length: About 12 cm. Diameter: About 12 mm by 9 mm. Color: 187A streaked with 187C. Cataphylls: Length: About 19 cm. Width, at base: About 5 cm. Shape: Triangular; keeled. Apex: Acutely pointed. Margin: Entire. Texture, upper and lower surfaces: Smooth, glabrous. Color, inner surface: 187B streaked with 187D. Color, outer surface: 187A streaked with 187C.

Inflorescence description:

*Inflorescence arrangement.*—Spathes and spadices arranged on upright scapes.

*Inflorescence longevity.*—Inflorescences last on the plant for about three months. Inflorescences persistent.

*Time to flower.*—Flowering occurs during the winter in Apopka, Fla.

*Spathe.*—Length: About 15 cm. Width: About 2.7 cm. Shape: Ovate. Apex: Pointed. Base: Cordate to obtuse. Margin: Entire. Texture, inner surface: Smooth, waxy, shiny. Texture, outer surface: Smooth, glossy. Color, inner and outer surfaces: 187A streaked with 187C.

*Spadix.*—Length: About 12.5 cm. Diameter: About 1.2 cm. Shape: Columnar, stout. Cross section: Rounded. Color, female flowers: 158B. Color, male flowers: 159D. Female flower diameter: About 1 to 2 mm. Quantity of female flowers per inflorescence: About 500.

*Scape.*—Length: About 3.5 cm. Diameter: About 1 cm. Color: 187A.

*Seed/fruit.*—Seed and fruit development on plants of the new *Philodendron* has not been observed.

Disease/pest resistance: Under commercial conditions, plants of the new *Philodendron* have not been observed to be resistant to pathogens or pests common to *Philodendron.*

Temperature tolerance: Plants of the new *Philodendron* have been observed to be tolerant to temperatures ranging from 0 to 40° C.

It is claimed:

1. A new and distinct cultivar of *Philodendron* plant named 'Variegated Sport #1', as illustrated and described.

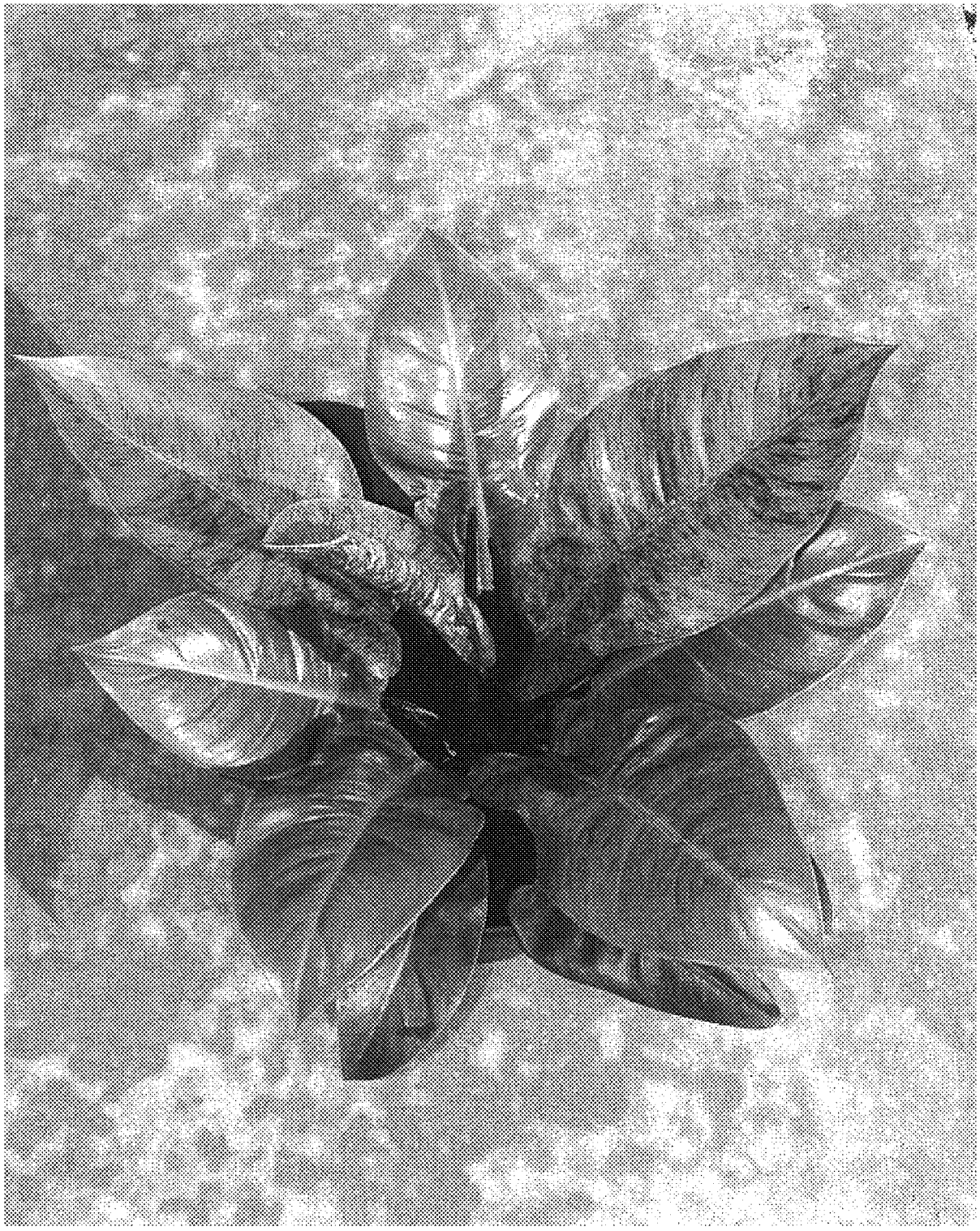

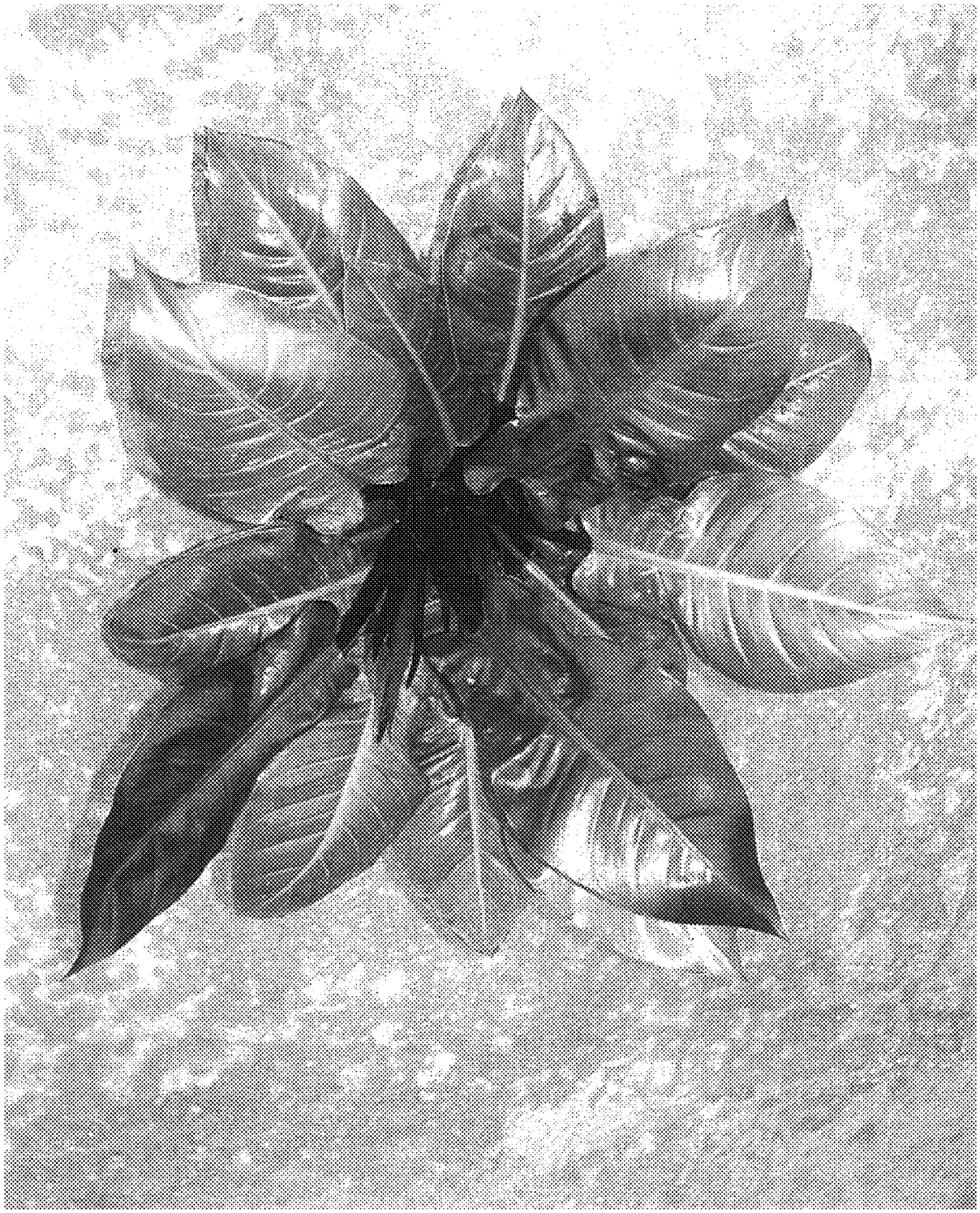

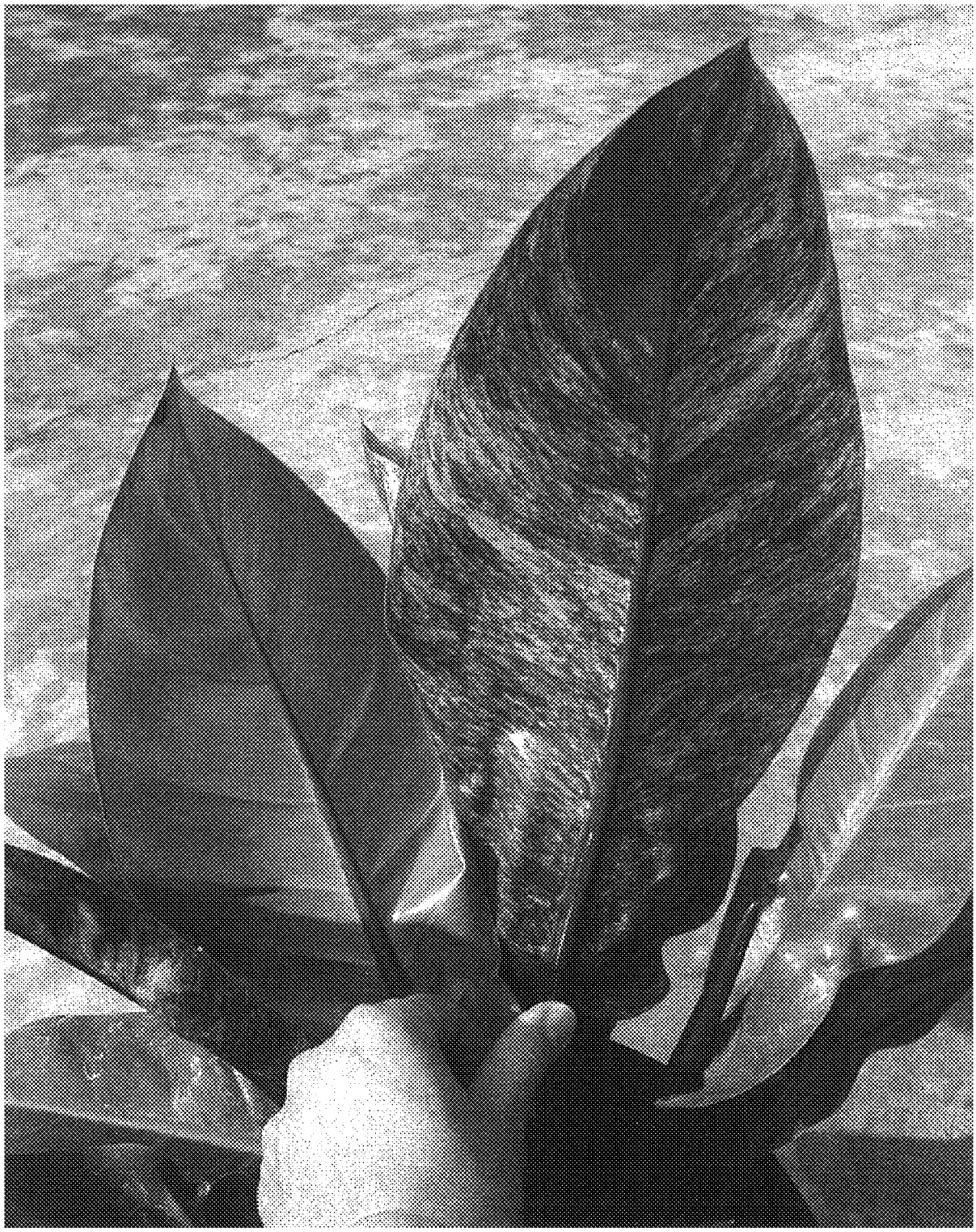

* * * * *